(12) United States Patent
Yamato et al.

(10) Patent No.: US 8,642,338 B2
(45) Date of Patent: Feb. 4, 2014

(54) ANTERIOR OCULAR SEGMENT RELATED CELL SHEETS, THREE-DIMENSIONAL STRUCTURES, AND PROCESSES FOR PRODUCING THE SAME

(75) Inventors: Masayuki Yamato, Tokyo (JP); Teruo Okano, Ichikawa (JP)

(73) Assignee: Cellseed Inc., Tokyo (JP)

( * ) Notice: Subject to any disclaimer, the term of this patent is extended or adjusted under 35 U.S.C. 154(b) by 603 days.

(21) Appl. No.: 10/544,542

(22) PCT Filed: Feb. 6, 2003

(86) PCT No.: PCT/JP03/01248
§ 371 (c)(1),
(2), (4) Date: Jun. 5, 2006

(87) PCT Pub. No.: WO2004/070023
PCT Pub. Date: Aug. 19, 2004

(65) Prior Publication Data
US 2006/0240552 A1 Oct. 26, 2006

(51) Int. Cl.
*C12N 11/08* (2006.01)
*C12N 5/00* (2006.01)
*C12N 5/02* (2006.01)

(52) U.S. Cl.
USPC ............ 435/402; 435/180; 435/378; 435/395

(58) Field of Classification Search
USPC .......................... 435/180, 378, 395, 401, 402
See application file for complete search history.

(56) References Cited

U.S. PATENT DOCUMENTS

| | | | |
|---|---|---|---|
| 4,780,409 A | 10/1988 | Monji et al. | |
| 5,284,766 A | 2/1994 | Okano et al. | |
| 5,962,324 A * | 10/1999 | O'Connor et al. | ............ 435/394 |
| 2003/0036196 A1 | 2/2003 | Okano et al. | |
| 2004/0009566 A1 | 1/2004 | Okano et al. | |
| 2004/0028657 A1 | 2/2004 | Okano et al. | |
| 2006/0234377 A1 | 10/2006 | Okano et al. | |
| 2006/0240552 A1 | 10/2006 | Yamato et al. | |
| 2007/0092492 A1 | 4/2007 | Matsuda et al. | |
| 2007/0148137 A1 | 6/2007 | Okano et al. | |
| 2008/0118474 A1 | 5/2008 | Okano et al. | |
| 2008/0131476 A1 | 6/2008 | Kanzaki et al. | |
| 2008/0226692 A1 | 9/2008 | Sato et al. | |
| 2008/0289052 A1 | 11/2008 | Okano et al. | |
| 2009/0011504 A1 | 1/2009 | Kataoka et al. | |
| 2010/0239498 A1 | 9/2010 | Ohashi et al. | |
| 2011/0229962 A1 | 9/2011 | Mizutani et al. | |
| 2012/0052524 A1 | 3/2012 | Kinooka et al. | |
| 2012/0107930 A1 | 5/2012 | Sasaki et al. | |
| 2012/0156781 A1 | 6/2012 | Takahashi et al. | |
| 2012/0210451 A1 | 8/2012 | Shimizu et al. | |

FOREIGN PATENT DOCUMENTS

| | | | |
|---|---|---|---|
| EP | 382214 | 8/1990 | |
| EP | 552380 | 7/1993 | |
| EP | 1264877 A1 | 12/2002 | |
| EP | 1602383 A1 | 12/2005 | |
| JP | 05-015583 | 1/1993 | |
| JP | 2001-161353 | * 6/2001 | ............... C12N 5/06 |
| WO | 01/68799 A1 | 9/2001 | |
| WO | 01/80760 | 11/2001 | |
| WO | WO 02/10349 A1 | 2/2002 | |
| WO | 2004/069295 A1 | 8/2004 | |
| WO | 2004/070023 A1 | 8/2004 | |
| WO | 2004/073761 A1 | 9/2004 | |

OTHER PUBLICATIONS

Masayuki Yamato et al. "Thermo-Responsive Culture Dishes Allow the Intact Harvest of Multilayered Keratinocyte Sheets without Dispase by Reducing Temperature" Tissue Engineering vol. 7, No. 4, 2001 p. 473 to 480.*
Nandkumar et al. "Two-dimensional cell sheet manipulation of heterotypically co-cultured lung cells utilizing temperature-responsive culture dishes results in long-term maintenance of differentiated epithelial cell functions" Biomaterials 23:1121-1130 (2002).
Okano et al., *Soshiki Kogaku ga Sasaeru Saibo Sheet Kogaku*, The Tissue Culture Engineering, Sep. 2001, vol. 27, No. 10, pp. 366-367.
Yamato et al., *Jinko Zairyo o Mochiita Saibo no Manipulation Saibo Sheet Kogaku no Sosei*, Protein Nucleic Acid and Enzynme, Sep. 2000, vol. 45, No. 13, pp. 2156-2161.
Int'l Preliminary Report on Patentability for PCT/JP2004/001975, Feb. 2006, six pages.
Partial translation of JP 2001-161353, "Cell graft for transplantation and method for preparing the same" Jun. 2001, eight pages.
Int'l Preliminary Report on Patentability for PCT/JP2003/001248, Aug. 2005, five pages.
Hirose et al. "Temperature-responsive surface for novel co-culture systems of hepatocytes with endothelial cells: 2-D patterned and double layered co-cultures" Yonsei Medical Journal 41:803-813 (2000).
Nishida "Tissue engineering of the cornea" Med. Sci. Dig. 28:577-581 (Dec. 2002) and its English translation.
Nishida "Tissue engineering for corneal epithelium and corneal endothelium" Nihon Biomateiral Gakkai 20:259-268 (Jul. 2002) and its English translation.
Ohji et al. "Corneal epithelium culturing on type IV collagen sheet" Folia Ophthalmogica Japonica 42:784-788 (1991) and English translation of abstract.

(Continued)

*Primary Examiner* — Thane Underdahl
(74) *Attorney, Agent, or Firm* — Nixon & Vanderhye PC

(57) ABSTRACT

An anterior ocular segment related cell sheet or three-dimensional structure that have only a few structural defects as they have been recovered retaining the intercellular desmosome structure and the basement membrane-like protein between cell and substrate. The anterior ocular segment related cell sheet or three-dimensional structure is produced by a process comprising the steps of cultivating cells on a cell culture support comprising a substrate having its surface covered with a temperature responsive polymer having an upper or lower critical dissolution temperature of 0-80° C. with respect to water, optionally stratifying the layer of cultured cells by the usual method, and thereafter, (1) adjusting the temperature of the culture solution to either above the upper critical dissolution temperature or below the lower critical dissolution temperature, and further optionally
(2) bringing the cultured anterior ocular segment related cell sheet or three-dimensional structure into close contact with a polymer membrane, and
(3) detaching the sheet or three-dimensional structure together with the polymer membrane.

13 Claims, No Drawings

(56) References Cited

OTHER PUBLICATIONS

Yamato et al. "Thermo-responsive culture dishes allow the intact harvest of multilayered keratinocyte sheets without dispase by reducing temperature" Tissue Eng. 7:473-480 (2001).
Nishida et al. "Functional bioengineered corneal epithelial sheet grafts from corneal stem cells expanded ex vivo on a temperature-responsive cell culture surface" Transplantation 77:379-385 (2004).
Tsubota et al. "Treatment of severe ocular-surface disorders with corneal epithelial stem-cell transplantation" New Engl. J. Med. 340:1697-1703 (1999).
Yamato et al. English translation of "Cell manipulation using artificial material creation of cell sheet engineering" Protein, Nucleic Acid and Enz. 45:2156-2161) (2000).
European Search Report for Application No. 10166489.4 dated Jul. 30, 2010.
Kinoshita "Ocular surface reconstruction by tissue engineering" *Nippon Ganka Gakkai Zasshi*, vol. 106, No. 12, pp. 837-868 (Dec. 2002).
Manu Examination Report for European Application No. 10182011.6, five pages, mailed Dec. 20, 2012.
Lindberg et al. "In vitro propagation of human ocular surface epithelial cells for transplantation" Invest. Ophthalmol. Vis. Sci. 34:2672-2679 (1993).

\* cited by examiner

ANTERIOR OCULAR SEGMENT RELATED CELL SHEETS, THREE-DIMENSIONAL STRUCTURES, AND PROCESSES FOR PRODUCING THE SAME

This application is the US national phase of international application PCT/JP2003/001248 filed 6 Feb. 2003, which designated the U.S., the entire contents of which is hereby incorporated by reference.

TECHNICAL FIELD OF THE INVENTION

This invention relates to anterior ocular segment related cell sheets and three-dimensional structures in biology, medicine and other fields, as well as processes for producing such sheets, and therapeutic methods using them.

BACKGROUND ART

With marked advances in medical technology, it has recently become popular to perform organ transplants, i.e., replacing a difficult-to-treat organ with another person's organ. The organs that can be transplanted are quite diverse and include the skin, cornea, kidney, liver and heart, and in addition, the postoperative progress of organ transplants has improved so remarkably that they are already becoming established as a medical procedure. Keratoplasty is one example and as early as 40 years ago, an eye bank was organized in Japan to start transplanting activities. However, as of today, the number of donors in Japan is very small and notwithstanding the fact that there are annually about 20,000 patients who need keratoplasty, only a tenth of them (ca. 2,000 in number) can actually be treated by that procedure. Although keratoplasty is a virtually established procedure, it suffers the problem of shortage in donors, giving rise to the need for the development of a next-generation medical procedure.

With this background, attention has been drawn to the procedure of directly transplanting artificial substitutes or cells that were cultured into assembly. Typical examples of this approach are the artificial skin and the cultured skin. However, the artificial skin using synthetic polymers has the potential to cause rejection and other side effects that make it undesirable as skin grafts. On the other hand, the cultured skin is prepared by cultivating a portion of the normal skin of the patient until it grows to a desired size, so it can be used without the risk of causing rejection and any other side effects and may well be described as the most natural masking agent.

Conventionally, such cell culture has been performed either on the surface of glass or on the surface of synthetic polymers that were subjected to a variety of treatments. For example, a variety of polystyrene vessels that were subjected to surface treatments such as y-ray irradiation and silicone coating have become popular for use in cell culture. Cells that have been cultivated to grow on those vessels for cell culture are detached and recovered from the surfaces of the vessels by treatment with proteinases such as trypsin or chemical reagents.

However, it has been pointed out that the recovery of grown cells by treatment with chemical reagents involves some disadvantages such as the processing steps becoming cumbersome to increase the chance of contamination by impurities and the grown cells becoming denatured or damaged by the chemical treatment to have their inherent functions injured. In order to overcome these disadvantages, several techniques have been proposed to date.

JP 2-23191 B describes a method for producing a transplantable membrane of keratin tissue which comprises the steps of cultivating human neonatal keratinized epidermic cells in a culture vessel under conditions that enable a membrane of keratin tissue to form on the surface of the vessel and detaching the membrane of keratin tissue using an enzyme. Specifically, with 3T3 cells used as a feeder layer, the epidermic cells are grown and stratified as a cell sheet which is recovered using the proteinase dispase. However, the method described in JP 2-23191 B has had the following defects.

(1) Dispase is of microbial origin and the recovered cell sheet needs to be washed thoroughly.
(2) The conditions for dispase treatment differ from one batch of cell culture to another and great skill is required in the treatment.
(3) The cultured epidermic cells are pathologically activated by dispase treatment.
(4) The extracellular matrix is decomposed by dispase treatment.
(5) As the result, the diseased site to which the cell sheet has been grafted is prone to infection.

However, anterior ocular segment related cells that are contemplated in the present invention, such as corneal epithelial cells, corneal endothelial cells and conjunctival epithelial cells, do not have as strong intercellular binding as dermal cells and it has been impossible to detach and recover cultivated cells as a single sheet even if the dispase is employed.

In order to solve this problem, a technique has recently been devised, according to which corneal epithelial cells or conjunctival epithelial cells are cultured into assembly on an amnion deprived of the spongy layer and the epithelial layer and the assembly is used as a cell graft together with the amnion (JP 2001-161353 A). Since the amnion has adequate strength as a membrane but has no antigenicity, it is favorable as a support of cell grafts; however, the amnion is not inherently in the eye and in order to construct a more precise intraocular tissue, it has been desired that a satisfactorily strong sheet be prepared solely from the intraocular cells.

The present invention has been accomplished with a view to solving the aforementioned problems of the prior art. Therefore, the present invention has as an object providing an anterior ocular segment related cell sheet or a three-dimensional structure that have only a few structural defects as they have been recovered retaining the intercellular desmosome structure and the basement membrane-like protein between cell and substrate. Another object of the present invention is to provide a process by which cultivated and grown cells can be detached and recovered from a substrate's surface easily and as a satisfactorily strong, single sheet by changing the ambient temperature without treatment with an enzyme such as dispase.

SUMMARY OF THE INVENTION

In order to attain the stated objects, the present inventors engaged in R&D activities taking various angles of study. As a result, the inventors found that an anterior ocular segment related cell sheet or three-dimensional structure having fewer structural defects could be obtained by a process comprising the steps of cultivating anterior ocular segment related cells on a cell culture support comprising a substrate having its surface covered with a temperature responsive polymer, optionally stratifying the layer of cultured cells, thereafter adjusting the temperature of the culture solution to either above an upper critical solution temperature or below a lower critical solution temperature, bringing the cultured anterior ocular segment related cell sheet or three-dimensional structure into close contact with a polymer membrane, and detaching the sheet or three-dimensional structure together with the polymer membrane. The present invention has been accomplished on the basis of this finding.

Thus, the present invention first provides an anterior ocular segment related cell sheet or three-dimensional structure that have only a few structural defects as they have been recovered retaining the intercellular desmosome structure and the basement membrane-like protein between cell and substrate.

The present invention also provides a process for producing an anterior ocular segment related cell sheet or three-dimensional structure, comprising the steps of cultivating cells on a cell culture support comprising a substrate having its surface covered with a temperature responsive polymer having an upper or lower critical solution temperature of 0-80° C. with respect to water, optionally stratifying the layer of cultured cells by the usual method, and thereafter, (1) adjusting the temperature of the culture solution to either above the upper critical solution temperature or below the lower critical solution temperature,
(2) bringing the cultured anterior ocular segment related cell sheet or three-dimensional structure into close contact with polymer membrane, and
(3) detaching the sheet or three-dimensional structure together with the polymer membrane.

In addition, the present invention provides a process for producing a three-dimensional structure by stratifying the anterior ocular segment related cell sheet or three-dimensional structure in close contact with polymer membrane as obtained by the process described in the foregoing paragraph, the stratification being effected by repeating the sequence of the steps of attaching said anterior ocular segment related cell sheet or three-dimensional structure to a cell culture support, with or without being covered on a surface with a temperature responsive polymer, a polymer membrane, another cell sheet, or the like, and thereafter stripping the polymer membrane out of close contact.

Further in addition, the present invention provides the above-described anterior ocular segment related cell sheet or three-dimensional structure for the treatment of a tissue that has become deficient and/or wounded to a deeper area.

Still further in addition, the present invention provides a method of treatment characterized in that the above-described anterior ocular segment related cell sheet or three-dimensional structure is grafted to a tissue that has become deficient and/or wounded to a deeper area.

Still further, the present invention provides an anterior ocular segment related cell sheet or three-dimensional structure that are useful not only in the medical field but also as cells for safety assessment of chemical substances, poisons or medicines.

BEST MODES FOR CARRYING OUT THE INVENTION

Cells that can suitably be used in the preparation of the anterior ocular segment related cell sheet or three-dimensional structure of the present invention include corneal epithelial cells, corneal endothelial cells, conjunctival epithelial cells, and epithelial stem cells but the applicable cells are by no limited in type. In the present invention, the anterior ocular segment related cell sheet means a sheet obtained by cultivating a single layer of the above-described various kinds of anterior ocular segment forming cells in the living body on a culture support and thereafter detaching the layer from the support; the three-dimensional structure means a sheet that is obtained by stratifying the above-described sheet of various cultured epithelial cells, either on its own or in combination with a sheet or sheets of other cells.

The anterior ocular segment related cell sheet or three-dimensional structure in the present invention is such that they have not been damaged during cultivation by proteinases typified by dispase and trypsin. Therefore, the anterior ocular segment related cell sheet or three-dimensional structure as detached from the substrate retains the intercellular desmosome structure, has only a few structural defects, and features high strength. This means that if the obtained anterior ocular segment related cell sheet or three-dimensional structure is applied for such purposes as grafting, the anterior ocular segment related cell sheet or three-dimensional structure of the present invention having sufficient strength helps the diseased site to be completely isolated from the outside. In addition, the sheet of the present invention is characterized in that the basement membrane-like protein formed between cell and substrate during cultivation has not been destroyed by enzyme. Hence, the sheet can attach satisfactorily to the living tissue of the diseased site to which it has been grafted and this enables an efficient treatment to be performed. This is described below more specifically. If an ordinary proteinase such as trypsin is employed, the intercellular desmosome structure and the basement membrane-like protein between cell and substrate are hardly retained and, hence, the cell sheet is detached with the cells separated into discrete masses. As for the proteinase dispase, it destroys almost all of the basement membrane-like protein between cell and substrate but the cell sheet can be detached with 10-60% of the intercellular desmosome structure being retained and yet the cell sheet obtained has only low strength. In contrast, the cell sheet of the present invention keeps at least 80% of each of the desmosome structure and the basement membrane-like protein intact, thus providing the various advantages described above.

As described above, the anterior ocular segment related cell sheet or three-dimensional structure in the present invention is a cell sheet that retains both the intercellular desmosome structure and the basement membrane-like protein between cell and substrate and which still features high strength; it has not been possible at all to obtain it by the prior art.

The temperature responsive polymer which is used to cover the substrate of the cell culture support is characterized by having an upper or lower critical solution temperature of 0° C. - 80° C., more preferably 20° C. - 50° C., in aqueous solution. If the upper or lower critical solution temperature exceeds 80° C., cells may die, which is not preferred. If the upper or lower critical solution temperature is below 0° C., the cell growth rate will generally drop by an extreme degree or cells will die, which also is not preferred.

The temperature responsive polymer to be used in the present invention may be a homopolymer or a copolymer. Examples of such polymers include the polymers described in JP 2-211865 A. Specifically, they are obtained by homo- or copolymerization of the following monomers. Monomers that can be used include, for example, (meth)acrylamide compounds, N-(or N,N-di)alkylsubstituted (meth)acrylamide derivatives, and vinyl ether derivatives; in the case of copolymers, any two or more of those monomers may be used. In addition, those monomers may be copolymerized with other monomers, or polymers may be grafted together or copolymerized, or alternatively, mixtures of polymers and copolymers may be employed. If desired, the polymers may be crosslinked to the extent that will not impair their properties.

The substrate that is to be covered with the temperature responsive polymer may be chosen from among the glass, modified glass, compounds such as polystyrene and poly (methyl methacrylate), and all other substances that can generally be given shape, as exemplified by polymer compounds other than those compounds, and ceramics.

The method of covering the support with the temperature responsive polymer is not limited in any particular way but one may follow the methods described in JP 2-211865 A. Specifically, the covering operation can be achieved by either subjecting the substrate and the above-mentioned monomers or polymers to electron beam (EB) exposure, γ-ray irradiation, ultraviolet irradiation, plasma treatment, corona treatment or organic polymerization reaction or by means of physical adsorption as effected by application of coating solutions or the kneading step.

The support material shown in the present invention is characterized by having two regions, region A covered with the temperature responsive polymer, and the following region B on its surface:
(1) a region covered with a polymer having less affinity for cells;
(2) a region covered with a different amount of the temperature responsive polymer than in region A;
(3) a region covered with a polymer responsive to a different temperature than in region A; or a combination of any two of regions (1)-(3) or a combination of the three.

The method of preparing the support material is not limited at all as long as the final product has the above-mentioned structures; to mention a few examples, they include (1) a method comprising the steps of first forming region B over the entire surface of the substrate and then superposing region A with the area masked which eventually serves as region B, or vice versa, (2) a method comprising the steps of covering the substrate with two layers of A and B and scraping either layer by an ultrasonic or scanning device, and (3) a method of offset printing the covering substances, which methods may be employed either alone or in combination.

The morphology of the covered regions are not limited in any way and may include the following patterns as seen above: (1) a combination of lines and spaces, (2) polka dots, (3) a grid, or patterns made of other special shapes, or patterns of their mixtures. Considering the state of each intraocular tissue, the pattern of dots (2) is preferred.

The size of the covered areas is not limited in any way but considering the size of each intraocular tissue and the possibility that a cultured anterior ocular segment related cell sheet or three-dimensional structure may shrink as they are detached from the support, the following can at least be said about a dotted pattern: if the cells within each dot are to be used, the dot diameter is generally no more than 5 cm, preferably no more than 3 cm, and more preferably 2 cm or less; if the cells outside each dot are to be used, the dot diameter is generally no more than 1 mm, preferably no more than 3 mm, and more preferably 5 mm or less.

The coverage of the temperature responsive polymer is suitably in the range of 0.3-6.0 $\mu g/cm^2$, preferably 0.5-3.5 $\mu g/cm^2$, more preferably 0.8-3.0 $\mu g/cm^2$. If the coverage of the temperature responsive polymer is less than 0.2 $\mu g/cm^2$, the cells on the polymer will not easily detach even if they are given a stimulus and the operating efficiency is considerably lowered, which is not preferred. If, on the other hand, the coverage of the temperature responsive polymer is greater than 6.0 $\mu g/cm^2$, cells will not easily adhere to the covered area and adequate adhesion of the cells becomes difficult to achieve.

The polymer having high affinity for cells as used in the present invention is not limited in any way as long as it is free from cell adherence; examples include hydrophilic polymers such as polyacrylamide, poly(dimethyl acrylamide), polyethylene glycol and celluloses, or highly hydrophobic polymers such as silicone polymers and fluoropolymers.

In the present invention, cell cultivation is effected on the cell culture support (e.g. cell culture dish) that has been prepared in the manner described above. The temperature of the culture medium is not limited in any particular way, except that it depends on whether the aforementioned polymer the substrate's surface has been covered with has an upper critical solution temperature or a lower critical solution temperature; in the former case, the medium's temperature should not be higher than the upper critical solution temperature and, in the latter case, it should not be less than the lower critical solution temperature. It goes without saying that it is inappropriate to perform cultivation in a lower-temperature range where the cultured cells will not grow or in a higher-temperature range where the cultured cells will die. The culture conditions other than temperature may be as adopted in the usual method and are not limited in any particular way. For instance, the culture medium to be used may be one that is supplemented with serum such as known fetal calf serum (FCS); alternatively, it may be a serum-free medium.

In the process of the present invention, the culture time may be set in accordance with the above-described method depending on the object of using the anterior ocular segment related cell sheet or three-dimensional structure. The cultured cells may be detached and recovered from the support material by first bringing the cultured anterior ocular segment related cell sheet or three-dimensional structure into close contact with the polymer membrane, then adjusting the temperature of the support material with adhering cells to either above the upper critical solution temperature of the overlying polymer on the support substrate or below its lower critical solution temperature, whereupon the cells can be detached together with the polymer membrane. Detachment of the anterior ocular segment related cell sheet or three-dimensional structure can be effected within the culture solution in which the cells have been cultivated or in other isotonic fluids, whichever is suitable depending on the object. The polymer membrane to be brought into close contact with the anterior ocular segment related cell sheet or three-dimensional structure may be exemplified by polyvinylidene difluoride (PVDF), polypropylene, polyethylene, celluloses, cellulose derivatives, chitin, chitosan, collagen, urethane, etc.

The method of producing the three-dimensional structure in the present invention is not limited in any particular way but may be exemplified by a method in which generally known 3T3 cells are grown as a feeder layer to effect stratification, or a method in which the cultured epithelial cell sheet in close contact with the aforementioned polymer membrane is utilized to produce the three-dimensional structure. The following specific methods may be mentioned as examples.
(1) The cell sheet in close contact with the polymer membrane is adhered to the cell culture support and, thereafter, the culture medium is added, whereby the polymer membrane is stripped from the cell sheet, to which another cell sheet in close contact with the polymer membrane is adhered, the process being repeated to form a stratified cell sheet.
(2) The cell sheet in close contact with the polymer membrane is inverted and fixed on the cell culture support, with the polymer membrane side facing down, and another cell sheet is adhered to the first cell sheet and, thereafter, the culture medium is added, whereby the polymer membrane is stripped from the cell sheet, to which yet another cell sheet is adhered, the process being repeated to form a stratified cell sheet.

(3) Two cell sheets, each in close contact with the polymer membrane, are held together in such a way that they face each other in close contact.

(4) A cell sheet in close contact with the polymer membrane is pressed against the diseased site of a living body so that it is adhered to the living tissue and, thereafter, the polymer membrane is stripped away and another cell sheet is superposed on the first cell sheet.

The three-dimensional structure of the present invention need not necessarily be made of corneal epithelial cells. It is also possible to overlie the cell sheet or three-dimensional structure made of corneal epithelial cells with a corneal endothelial cell sheet and/or a conjunctival epithelial cell sheet that have been prepared by following the same procedure. This procedure is extremely effective for the purpose of creating a structure closer to anterior ocular segment tissues in the living body.

In order to detach and recover the anterior ocular segment related cell sheet or three-dimensional structure with high yield, the cell culture support may be lightly tapped or rocked or the culture medium may be agitated with the aid of a pipette; these and other methods may be applied either independently or in combination. In addition, the cultured cells may optionally be washed with an isotonic fluid or the like so that they are detached for recovery.

The anterior ocular segment related cell sheet or three-dimensional structure obtained by the process described above far excels what are obtained by the prior art methods in terms of both easy detachment and high degree of non-invasiveness and have a great potential in clinical applications, as exemplified by corneal grafts. In particular, unlike the conventional graft sheets, the three-dimensional structure of anterior ocular segment related cells according to the present invention retains the basement membrane-like protein, so even if the diseased tissue to which it is going to be grafted is scraped by great thickness, the three-dimensional structure of the invention will take effectively. This contributes not only to improving the efficiency of treatment of the diseased site but also to reducing the burden on the patient, hence, it is anticipated to materialize as a very effective technique. Note that the cell culture support used in the process of the present invention allows for repeated use.

EXAMPLES

On the following pages, the present invention is described in greater detail by reference to examples which are by no means intended to limit the scope of the invention.

Examples 1 and 2

To a commercial polystyrene cell culture dish (FALCON 3001 petri-dish with a diameter of 3.5 cm manufactured by Beckton Dickinson Labware), a coating solution having N-isopropylacrylamide monomer dissolved in isopropyl alcohol to give a concentration of 40% (Example 1) or 50% (Example 2) was applied in a volume of 0.10 ml. Placed on the coated surface of the Petri-dish was a metallic mask having a diameter of 3.5 cm with a center hole having a diameter of 2 cm. While being kept in that state, the surface of the culture dish was exposed to electron beams with an intensity of 0.25 MGy, whereupon an N-isopropylacrylamide polymer (PIPAAm) was immobilized in a circular form (as an island, with the area under the mask being left as the sea which was covered with nothing since it was not exposed to electron beams). Then, the metallic mask was removed and a coating solution having N-isopropylacrylamide monomer dissolved in isopropyl alcohol to give a concentration of 20% was applied in a volume of 0.10 ml. This time, a circular metallic mask having a diameter of 2 cm was placed just to cover the circular area. While being kept in that state, the culture dish was exposed to electron beams with an intensity of 0.25 MGy, whereupon an acrylamide polymer was immobilized outside the circular PIPAAm layer. After the irradiation, the metallic mask was removed and the culture dish was washed with ion-exchanged water to remove the residual monomer and the PIPAAm that did not bind to the culture dish; the culture dish was then dried in a clean bench and sterilized with an ethylene oxide gas to provide a cell culture support material. The coverage of PIPAAm in the island area was determined from a cell culture support material prepared under identical conditions to the above except that no mask was used. As the result, it was found that under the conditions employed, the substrate's surface was covered with the temperature responsive polymer in an amount of 1.6 $\mu g/cm^2$ (Example 1) or 2.2 $\mu g/cm^2$ (Example 2). On the obtained cell culture support material, normal rabbit corneal epithelial cells were cultivated by the usual method (medium used: CORNEPAK (product of KURABO INDUSTRIES, LTD.); 37° C. under 5% $CO_2$). As it turned out, each of the cell culture support materials was such that the corneal epithelial cells adhered and grew normally in the central circular area. At day 14 of the culture, a 2 $cm^\Phi$ polyvinylidene difluoride (PVDF) membrane was placed over the cultivated cells and the culture medium, as gently aspirated, was subjected to incubating and cooling at 20° C. for 30 minutes together with the cell culture support material, whereupon the cells on each of the cell culture support materials were detached together with the overlying membrane. The overlying membrane could be easily stripped from each of the cell sheets. The cell sheets thus detached retained the intercellular desmosome structure and the basement membrane-like protein between cell and substrate and had adequate strength as a single sheet.

In each of Examples 1 and 2, "low-temperature treatment" was performed by incubating at 20° C. for 30 minutes but the "low-temperature treatment" to be performed in the present invention is not limited to the above-indicated temperature and time. The preferred temperature condition for the "low-temperature treatment" which is to be performed in the present invention is in the range of 0° C.-30° C. and the preferred treatment time is in the range from two minutes to an hour.

Example 3

By repeating the procedure of Example 1, normal rabbit corneal epithelial cells were cultivated on the same cell culture support, except that the medium was changed to the ordinary medium of Green et al. containing mitomycin C (DMEM+AB (for making a feeder layer): for human neonatal keratinized epithelial cells). As the result, the corneal epithelial cells on the cell culture support material adhered and grew normally in the central circular area, and the cell layer even stratified. At day 16 of the culture, the cells were incubated and cooled at 20° C. for 30 minutes together with the cell culture support material, whereupon the stratified, corneal epithelial cell sheet was detached. The stratified corneal epithelial cell sheet (three-dimensional structure) as detached was circular in shape and retained the intercellular desmosome structure and the basement membrane-like protein between cell and substrate to have adequate strength as a single sheet.

Comparative Examples 1 and 2

Cell culture support materials were prepared as in Example 1, except that the monomer solution for preparing the cell culture support in Example 1 was adjusted to 5% (Comparative Example 1) or 60% (Comparative Example 2). The resulting coverage on the cell culture supports was respectively 0.1 μg/cm$^2$ (Comparative Example 1) and 6.2 μg/cm$^2$ (Comparative Example 2). Thereafter, normal rabbit corneal epithelial cells were cultivated by the same procedure as Example 1 and an attempt was made to detach them. As it turned out, the cells on the support of Comparative Example 1 were difficult to detach even if they were given the low-temperature treatment; on the other hand, cells were difficult to adhere to the support of Comparative Example 2 and, hence, it was difficult to grow them satisfactorily. Thus, neither of the comparative cell culture supports was preferred as a cell substrate.

Example 4

Corneal endothelial cells were recovered from a rabbit's cornea by the usual method. The culture dish of Example 1 which had been grafted with polyisopropylamide (PIPAAm) was inoculated with those cells at a cell density of 2×10$^6$ cells/cm$^2$ and cultivation was performed by the usual method (medium used: DMEM containing 10% fetal calf serum; 37° C. under 5% CO$_2$). Again, the corneal endothelial cells normally adhered and grew only in the central circular area. Ten days later, it was confirmed that the corneal endothelial cells had become confluent; thereafter, as in Example 1, a 2 cm$^\Phi$ polyvinylidene difluoride (PVDF) membrane was placed over the cultivated cells and the culture medium, as gently aspirated, was subjected to incubating and cooling at 20° C. for 30 minutes together with the cell culture support material, whereupon the cells were detached together with the overlying membrane. The overlying membrane could be easily stripped from the cell sheet. The cell sheet thus detached retained the intercellular desmosome structure and the basement membrane-like protein between cell and substrate and had adequate strength as a single sheet.

Example 5

The procedure of Example 2 for preparing a cell culture support material was repeated, except that a circular metallic mask having a diameter of 2 cm was put in the center of the culture dish, PIPAAm was immobilized around the mask, then a metallic mask with a center hole having a diameter of 2 cm was overlaid, thereby making a cell culture support material having the polyacrylamide immobilized in the central area (as in Example 1, except that the inner polymer layer was placed outside and the outer polymer layer, inside). The coverage of PIPAAm outside the hole was 2.1 μg/cm$^2$. Subsequently, corneal endothelial cells were recovered from a rabbit's cornea by the usual method. The culture dish of Example 1 which had been grafted with polyisopropylamide (PIPAAm) was inoculated with those cells at a cell density of 2×10$^6$ cells/cm$^2$ and cultivation was performed by the usual method (medium used: DMEM containing 10% fetal calf serum; 37° C. under 5% CO$_2$). Again, the corneal endothelial cells normally adhered and grew only in the central circular area. Ten days later, it was confirmed that the corneal endothelial cells had become confluent; thereafter, as in Example 1, a 2 cm$^\Phi$ polyvinylidene difluoride (PVDF) membrane was placed over the cultivated cells and the culture medium, as gently aspirated, was subjected to incubating and cooling at 20° C. for 30 minutes together with the cell culture support material, whereupon the cells were detached together with the overlying membrane. The overlying membrane could be easily stripped from the cell sheet. The cell sheet thus detached retained the intercellular desmosome structure and the basement membrane-like protein between cell and substrate and had adequate strength as a single sheet.

Example 6

The corneal epithelial cell sheet on the culture dish of Example 2 from which the medium had been gently removed without cooling was immediately overlaid with the corneal epithelial cell sheet detached in Example 1. Thereafter, the culture medium used in Example 3 was gently placed to detach the polymer membrane out of close contact with the cell sheet. Kept this way, the cells were cultivated for 2 days to make a stratified sheet (three-dimensional structure) of corneal epithelial cells. The stratified sheet of corneal epithelial cells was given the same low-temperature treatment as in Example 3, whereupon it was detached from the surface of the support. The stratified sheet (three-dimensional structure) of corneal epithelial cells as detached had satisfactory strength as a single sheet.

Example 7

The corneal endothelial cell sheet on the culture dish of Example 4 from which the medium had been gently removed without cooling was immediately overlaid with the stratified sheet of corneal epithelial cells that was detached in Example 3. Thereafter, the culture medium used in Example 3 was gently placed to detach the polymer membrane out of close contact with the cell sheet. Kept this way, the cells were cultivated for 2 days to make a stratified sheet (three-dimensional structure) of corneal epithelial cells having the corneal endothelial cell layer. The stratified sheet of corneal epithelial cells was given the same low-temperature treatment as in Example 3, whereupon it was detached from the surface of the support. The detached three-dimensional structure, retaining the intercellular desmosome structure and the basement membrane-like protein between cell and substrate, had satisfactory strength as a single sheet.

Example 8

The corneal endothelial cell sheet on the culture dish of Example 4 from which the medium had been gently removed without cooling was fed with a 5% IV type, dissolved collagen containing medium (the same as the medium used in Example 4, except that it contained collagen) and left to stand as such for 20 minutes. Thereafter, the medium was again gently removed without cooling. The remaining corneal endothelial cell sheet on the culture dish was immediately overlaid with the stratified sheet of corneal epithelial cells that was detached in Example 3. Thereafter, the culture medium used in Example 3 was gently placed to detach the polymer membrane out of close contact with the cell sheet. Kept this way, the cells were cultivated for 2 days to make a stratified sheet (three-dimensional structure) of corneal epithelial cells having the corneal endothelial cell layer. The stratified sheet of corneal epithelial cells was given the same low-temperature treatment as in Example 3, whereupon it was detached from the surface of the support. The detached three-dimensional structure had satisfactory strength as a single sheet.

Example 9

The perforated, conjunctival epithelial cell sheet on the culture dish of Example 5 from which the medium had been gently removed without cooling was immediately overlaid partly with the stratified sheet (three-dimensional structure) of corneal epithelial cells having the corneal endothelial cell layer that was detached in Example 7. Thereafter, the culture medium used in Example 3 was gently placed to detach the polymer membrane out of close contact with the cell sheet. Kept this way, the cells were cultivated for 2 days to make a stratified sheet (three-dimensional structure) of corneal epithelial cells having the corneal endothelial cell layer to which the conjunctival epithelial cell sheet had adhered. The obtained three-dimensional structure was given the same low-temperature treatment as in Example 3, whereupon it was detached from the surface of the support. The detached three-dimensional structure had satisfactory strength as a single sheet.

Example 10

The stratified sheet (three-dimensional structure) of corneal epithelial cells obtained in Example 3 was grafted to a rabbit deficient of a corneal epithelial cell portion in accordance with the usual method. After grafting, the stratified sheet of corneal epithelial cells was sutured to the wound site. About 3 weeks later, the suture was removed and the stratified sheet of corneal epithelial cells had took well on the eyeball.

From the foregoing results, it became clear that using the procedure of the present invention, one can fabricate satisfactorily strong sheets solely from intraocular cells. This is believed to provide a very effective technique for reducing the burden on patients by making the treatment protocol more efficient, and for constructing even more precise tissues.

INDUSRTIAL APPLICABILITY

The anterior ocular segment related cell sheets or three-dimensional structures of the present invention will not decompose E-cadherin or laminin 5, as opposed to the case of dispase treatment, and yet they have extremely small numbers of structural defects, thus having a great potential for use in clinical applications including skin grafting. Hence, the present invention will prove very useful in medical and biological fields such as cell engineering and medical engineering.

The invention claimed is:

1. An in vitro anterior ocular segment comprising a cell sheet having at least 80% of both intercellular desmosome structure and basement membrane-like protein intact produced by a process comprising:
   (a) culturing cells selected from the group consisting of corneal epithelial cells, corneal endothelial cells, conjunctival epithelial cells, and epithelial stem cells on a cell culture support to form a cell sheet, wherein the surface of said cell culture support is covered with a temperature responsive polymer with an upper or lower critical solution temperature between 0-80° C. in an aqueous solution and wherein coverage of the temperature responsive polymer on the surface of said cell culture support is in the range of 0.3-6.0 µg/cm$^2$;
   (b) contacting the cell sheet from (a) with a polymer membrane on the opposite side from said cell culture support until the cell sheet adheres to the polymer membrane, wherein the polymer membrane is capable of being easily stripped from the cell sheet after adherence and wherein the polymer membrane is selected from the group consisting of polyvinylidene difluoride (PVDF), polypropylene, polyethylene, cellulose, cellulose derivatives, chitin, chitosan, collagen, and urethane;
   (c) detaching from said cell culture support the cell sheet with the polymer membrane adhered thereto from (b) by either increasing the temperature above the upper critical dissolution temperature or decreasing the temperature below the lower critical dissolution temperature, wherein the detaching is without subjecting the cell sheet or said cell culture support to any treatment with a proteinase; and
   (d) stripping the polymer membrane from the cell sheet from (c) to obtain a cell sheet having at least 80% of both intercellular desmosome structure and basement membrane-like protein intact.

2. A method of treatment, the method comprising grafting the anterior ocular segment according to claim 1 to a diseased site in which part or all of an anterior ocular segment tissue has been damaged or become deficient.

3. A process for producing an in vitro anterior ocular segment comprising a cell sheet having at least 80% of both intercellular desmosome structure and basement membrane-like protein intact, comprising:
   (a) cultivating cells selected from the group consisting of corneal epithelial cells, corneal endothelial cells, conjunctival epithelial cells, and epithelial stem cells on a cell culture support, wherein the surface of said cell culture support is covered with a temperature responsive polymer having an upper or lower critical dissolution temperature of 0-80° C. in aqueous solution and wherein coverage of the temperature responsive polymer on the surface of said cell culture support is in the range of 0.3-6.0 µg/cm$^2$, to form one or more layers of cells;
   (b) optionally stratifying the one or more layers of cells from (a) with another layer of cells, thereafter;
   (c) contacting the one or more layers of cells from (a) or stratified layers thereof from (b) with an overlaid polymer membrane until the one or more layers of cells or stratified layers thereof adheres to the polymer membrane, wherein the polymer membrane is capable of being easily stripped from the one or more layers of cells or stratified layers thereof after adherence and wherein the polymer membrane is selected from the group consisting of polyvinylidene difluoride (PVDF), polypropylene, polyethylene, cellulose, cellulose derivatives, chitin, chitosan, collagen, and urethane;
   (d) detaching from said cell culture support the one or more layers of cells or stratified layers thereof together with the polymer membrane adhered thereto from (c) by either increasing the temperature above the upper critical dissolution temperature or decreasing the temperature below the lower critical dissolution temperature, wherein the detaching is without subjecting the one or more layers of cells or stratified layers thereof or said cell culture support to any treatment with a proteinase; and
   (e) stripping the polymer membrane from the one or more layers of cells or stratified layers thereof from (d) to obtain a cell sheet having at least 80% of both intercellular desmosome structure and basement membrane-like protein intact.

4. The process for producing anterior ocular segment according to claim 3, wherein the cell culture support comprises a material having two regions, wherein the two regions are region A covered with the temperature responsive polymer and region B covered with one selected from the group consisting of:
- (i) a polymer having less affinity for cells,
- (ii) a different amount of the temperature responsive polymer than in region A,
- (iii) a polymer responsive to a different temperature than in region A,
- (iv) a combination of any two of regions (i) to (iii), and
- (v) a combination of all three of regions (i) to (iii).

5. The process for producing anterior ocular segment according to claim 3, which comprises again attaching in superposition the anterior ocular segment to a cell culture support, with or without being covered on a surface with a temperature responsive polymer, a polymer membrane, or alternatively attaching in superposition, either partly or entirely, the anterior ocular segment to another cell sheet.

6. The process for producing anterior ocular segment according to claim 3, wherein the temperature responsive polymer is poly(N-isopropylacrylamide).

7. The process for producing anterior ocular segment according to claim 3, wherein the polymer membrane is made of polyvinylidene difluoride rendered hydrophilic.

8. The process for producing anterior ocular segment according to claim 5, wherein the another cell sheet is at least one member selected from the group consisting of corneal epithelial cell sheet, stratified sheet of corneal epithelial cells, corneal endothelial cell sheet, and conjunctival epithelial cell sheet.

9. An in vitro anterior ocular segment which is produced by the process according to claim 3.

10. The anterior ocular segment according to claim 9, wherein the cells are stratified by cultivating corneal epithelial cells in layers.

11. The anterior ocular segment according to claim 9 which is a combination of at least (i) a corneal epithelial cell sheet with corneal endothelial cells or (ii) a stratified corneal epithelial cell sheet with corneal endothelial cells.

12. The anterior ocular segment according to claim 9 which is a combination of at least a corneal epithelial cell sheet or a stratified product thereof with corneal endothelial cells and conjunctival epithelial cells.

13. A method of treatment, the method comprising grafting the anterior ocular segment according to claim 9 to a diseased site in which part or all of an anterior ocular segment tissue has been damaged or become deficient.

* * * * *

UNITED STATES PATENT AND TRADEMARK OFFICE
CERTIFICATE OF CORRECTION

PATENT NO. : 8,642,338 B2  Page 1 of 1
APPLICATION NO. : 10/544542
DATED : February 4, 2014
INVENTOR(S) : Yamato et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 163 days.

Signed and Sealed this
Twenty-ninth Day of September, 2015

Michelle K. Lee
*Director of the United States Patent and Trademark Office*